United States Patent [19]
Robertson et al.

[11] Patent Number: 5,799,857
[45] Date of Patent: Sep. 1, 1998

[54] CIRCULAR ANASTOMOSIS DEVICE

[75] Inventors: John Charles Robertson, Bloomfield; Frank J. Viola, Sandy Hook, both of Conn.

[73] Assignee: United States Surgical Corporation, Norwalk, Conn.

[21] Appl. No.: 585,828

[22] Filed: Jan. 16, 1996

Related U.S. Application Data

[63] Continuation of Ser. No. 133,485, Oct. 7, 1993, abandoned.

[51] Int. Cl.$^6$ ............ A61B 17/064; A61B 17/115
[52] U.S. Cl. ............ 227/179.1; 227/19; 227/175.2
[58] Field of Search ............ 227/19, 179.1, 227/175.1, 175.2, 175.3, 176.1, 181.1

[56] References Cited

U.S. PATENT DOCUMENTS

| | | |
|---|---|---|
| 3,193,165 | 7/1965 | Akhalaya et al. . |
| 3,269,630 | 8/1966 | Fleischer .................. 227/19 X |
| 3,388,847 | 6/1968 | Kasulin et al. . |
| 3,593,903 | 7/1971 | Astafiev et al. . |
| 4,319,576 | 3/1982 | Rothfuss . |
| 4,351,466 | 9/1982 | Noiles . |
| 4,485,817 | 12/1984 | Swiggett . |
| 4,505,272 | 3/1985 | Utyamyshev et al. . |
| 4,576,167 | 3/1986 | Noiles . |
| 4,603,693 | 8/1986 | Conta . |
| 4,606,343 | 8/1986 | Conta et al. . |
| 4,646,745 | 3/1987 | Noiles . |
| 4,700,703 | 10/1987 | Resnick et al. . |
| 4,752,024 | 6/1988 | Green et al. . |
| 4,817,847 | 4/1989 | Redtenbacher et al. . |
| 5,005,749 | 4/1991 | Aranyi . |
| 5,104,025 | 4/1992 | Main et al. . |
| 5,119,983 | 6/1992 | Green . |
| 5,197,648 | 3/1993 | Gingold . |
| 5,205,459 | 4/1993 | Brinkerhoff et al. . |
| 5,271,543 | 12/1993 | Grant et al. . |
| 5,271,544 | 12/1993 | Fox et al. . |
| 5,332,142 | 7/1994 | Robinson et al. .............. 227/19 X |

FOREIGN PATENT DOCUMENTS

| | | |
|---|---|---|
| 8654764 | 9/1986 | Australia . |
| 0270260 | 8/1988 | European Pat. Off. . |
| 0449394 | 10/1991 | European Pat. Off. . |
| 0503689 | 9/1992 | European Pat. Off. . |
| 0536882 | 4/1993 | European Pat. Off. . |
| 0591999 | 4/1994 | European Pat. Off. . |
| 1121673 | 7/1968 | United Kingdom . |

*Primary Examiner*—Rinaldi I. Rada
*Assistant Examiner*—Boyer Ashley

[57] ABSTRACT

A surgical instrument is disclosed which includes a housing having proximal and distal end portions, a shaft extending from the housing distal end portion, the shaft having proximal and distal end portions, a fastener carrying cartridge positioned at the shaft distal end portion, the cartridge having a plurality of fasteners disposed therein, a fastener firing member operatively associated with the fastener carrying cartridge, at least one lever extending from the housing, the lever being adapted to move the fastener firing member to expel the fasteners from the cartridge, an anvil member disposed opposite the cartridge, an elongated member operatively associated with the anvil member for moving the anvil member relative to the cartridge, and a locking element disposed within the housing for locking the elongated member, and, therefore the anvil member, the locking element being movable between at least a first position and a second position such that when the locking element is in the first position the elongated member is movable and when the locking element is in the second position the elongated member is prevented from moving.

39 Claims, 5 Drawing Sheets

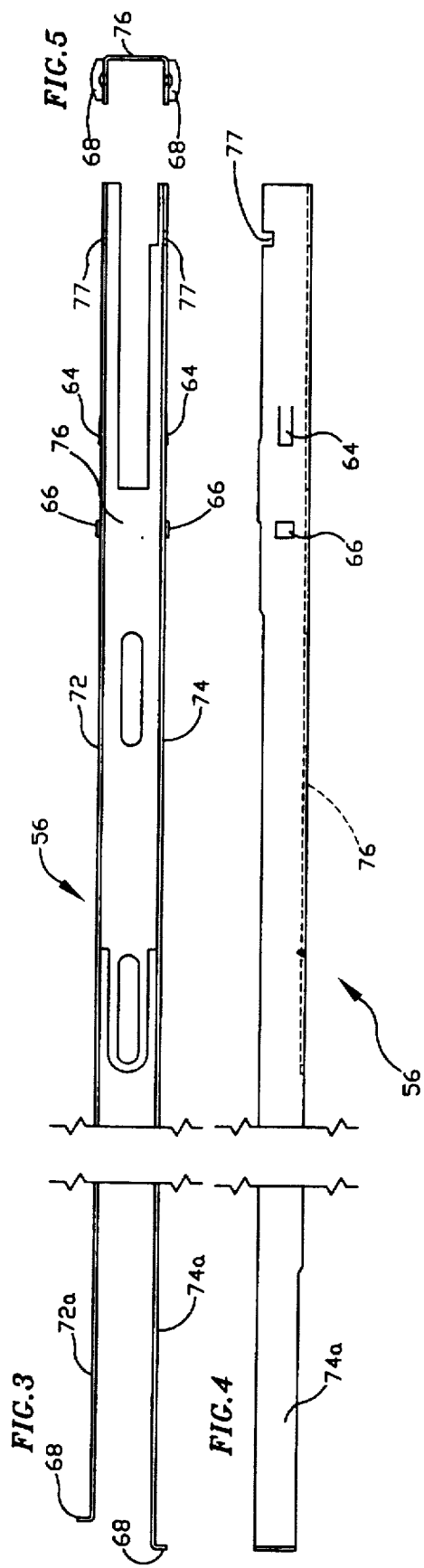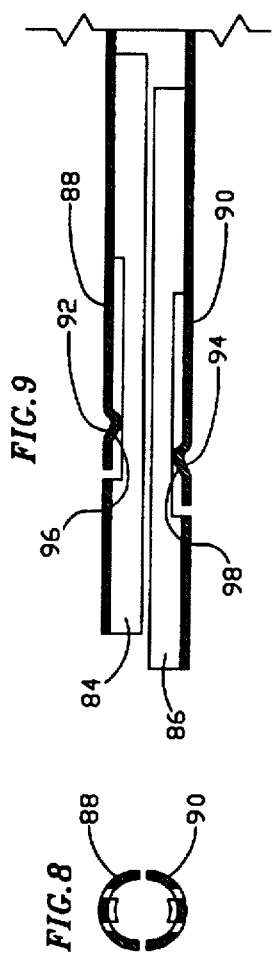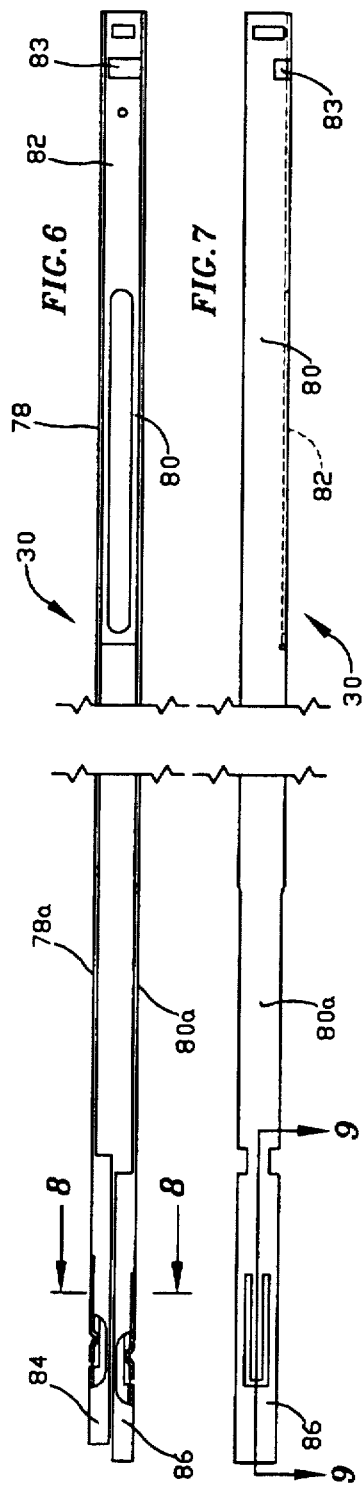

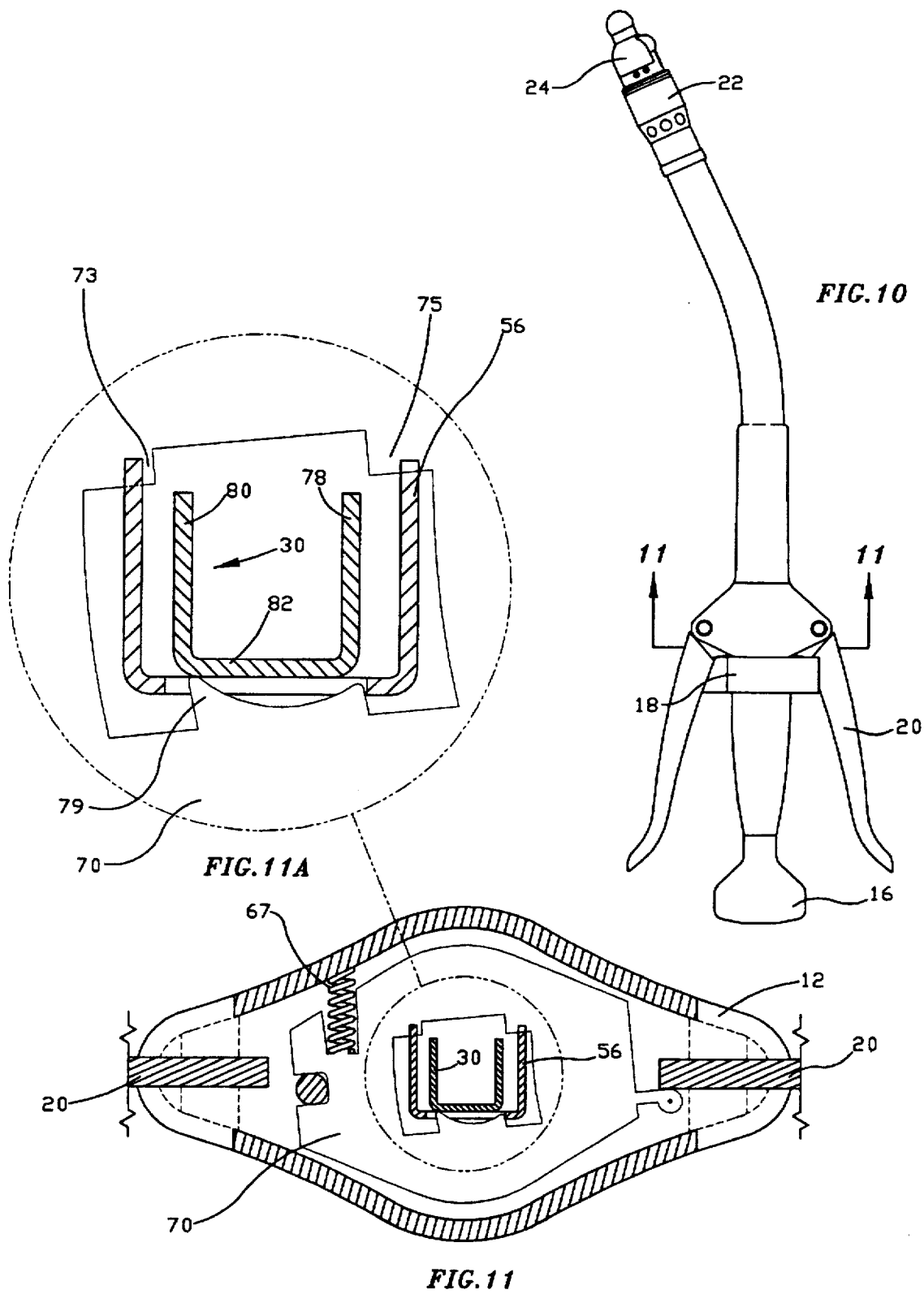

CIRCULAR ANASTOMOSIS DEVICE

This is a continuation of application Ser. No. 08/133,485 filed on Oct. 7, 1993, now abandoned.

BACKGROUND OF THE INVENTION

1. Field of the Invention

This invention relates to a surgical fastener applying instrument. More particularly, this invention relates to an arrangement for a circular anastomosis surgical stapling instrument.

2. Description of the Related Art

Various types of surgical fastener applying instruments have been known for the application of surgical fasteners to tissue. For example, it has been known to use various types of surgical staplers in gastric and esophageal surgery in both classic or modified gastric reconstructions performed end-to-end, end-to-side or side-to-side. In many cases, instruments, such as described in U.S. Pat. No. 4,603,693, have been used where an anvil assembly mounted on the end of a center rod can be manipulated relative to a staple assembly on the end of a tubular housing of the instrument. In instruments of this nature, the center rod is connected with a mechanism, for example, which employs a wing nut at the proximal end of the instrument, so that the rod can be moved back and forth independently of the staple assembly so as to adjust the anvil assembly relative to the staple assembly. Likewise, a pusher tube is mounted within the instrument for movement via a handle mechanism so as to cause a firing of the staples from the staple assembly towards the anvil assembly.

In some instruments, such as described in U.S. Pat. No. 4,351,466, these stapling instruments have been provided with a pair of handles in order to actuate the pusher tube to cause a firing of the staples. In such cases, each handle has been pivotally mounted so as to be moved toward the other handle during manual squeezing by a surgeon. Each handle also includes a lever arm within the instrument which engages against the pusher tube so as to move the tube in a proximal direction.

Stapling instruments of this type have also been provided with safety locks in order to prevent the squeezing together of the handles prematurely. That is, the safety locks have been provided in order to prevent the handles from moving towards each other before a surgeon has manipulated the anvil assembly into position for the firing of the staples. While these instruments have been used safely and effectively for years, it would be advantageous to provide the feature of preventing the anvil member from being able to be moved once a fastener firing safety lock has been released. Also a continuing need exists to develop these types of surgical stapling instruments which require fewer parts and materials to manufacture, thereby reducing costs of production and requiring less labor to assemble the parts. Additionally, if the instruments are disposable, i.e. single use only, use of less materials is desirable to decrease the amount of medical waste generated during a surgical procedure.

SUMMARY OF THE INVENTION

The present invention provides a surgical fastener applying instrument which includes a novel anvil lockout mechanism which works in cooperation with the safety release mechanism for the fastener firing member. The instrument of the present invention is lightweight and easy to manufacture. It requires fewer component parts than similar available instruments and, therefore, is less costly to produce.

The surgical instrument includes a housing having proximal and distal end portions, a shaft extending from the housing distal end portion, the shaft having proximal and distal end portions, a fastener carrying cartridge positioned at the shaft distal end portion, the cartridge having a plurality of fasteners disposed therein, a fastener firing member operatively associated with the fastener carrying cartridge, at least one lever extending from the housing, the lever being adapted to move the fastener firing member to expel the fasteners from the cartridge, an anvil member disposed opposite the cartridge, an elongated member operatively associated with the anvil member for moving the anvil member relative to the cartridge, and locking means disposed within the housing for locking the elongated member, and, therefore the anvil member, the locking means being movable between at least a first position and a second position such that when the locking means is in the first position the elongated member is movable and when the locking means is in the second position the elongated member is prevented from moving.

In a preferred embodiment the locking means is operatively associated with a safety mechanism for preventing movement of the at least one lever, the safety mechanism being movable between at least a first position and a second position.

BRIEF DESCRIPTION OF THE DRAWINGS

Preferred embodiments of the invention are described hereinbelow with reference to the drawings wherein:

FIG. 3 is a top plan view of the fastener firing member of the present invention;

FIG. 4 is a side plan view of the fastener firing member;

FIG. 5 is an end view of the fastener firing member;

FIG. 6 is a top plan view of the elongated member for moving the anvil of the present invention relative to the stapling cartridge;

FIG. 7 is a side plan view of the elongated member of FIG. 6;

FIG. 8 is a cross-sectional view taken along section line 8—8 of FIG. 6;

FIG. 9 is a cross-sectional view taken along section line 9—9 of FIG. 7;

FIG. 10 is a plan view of the instrument showing the lever members in the unfired position;

FIG. 11 is a cross-sectional view taken along section line 11—11 of FIG. 10;

FIG. 11A is an enlarged view of the area indicated in FIG. 11;

DETAILED DESCRIPTION OF THE PREFERRED EMBODIMENTS

Figure 1:
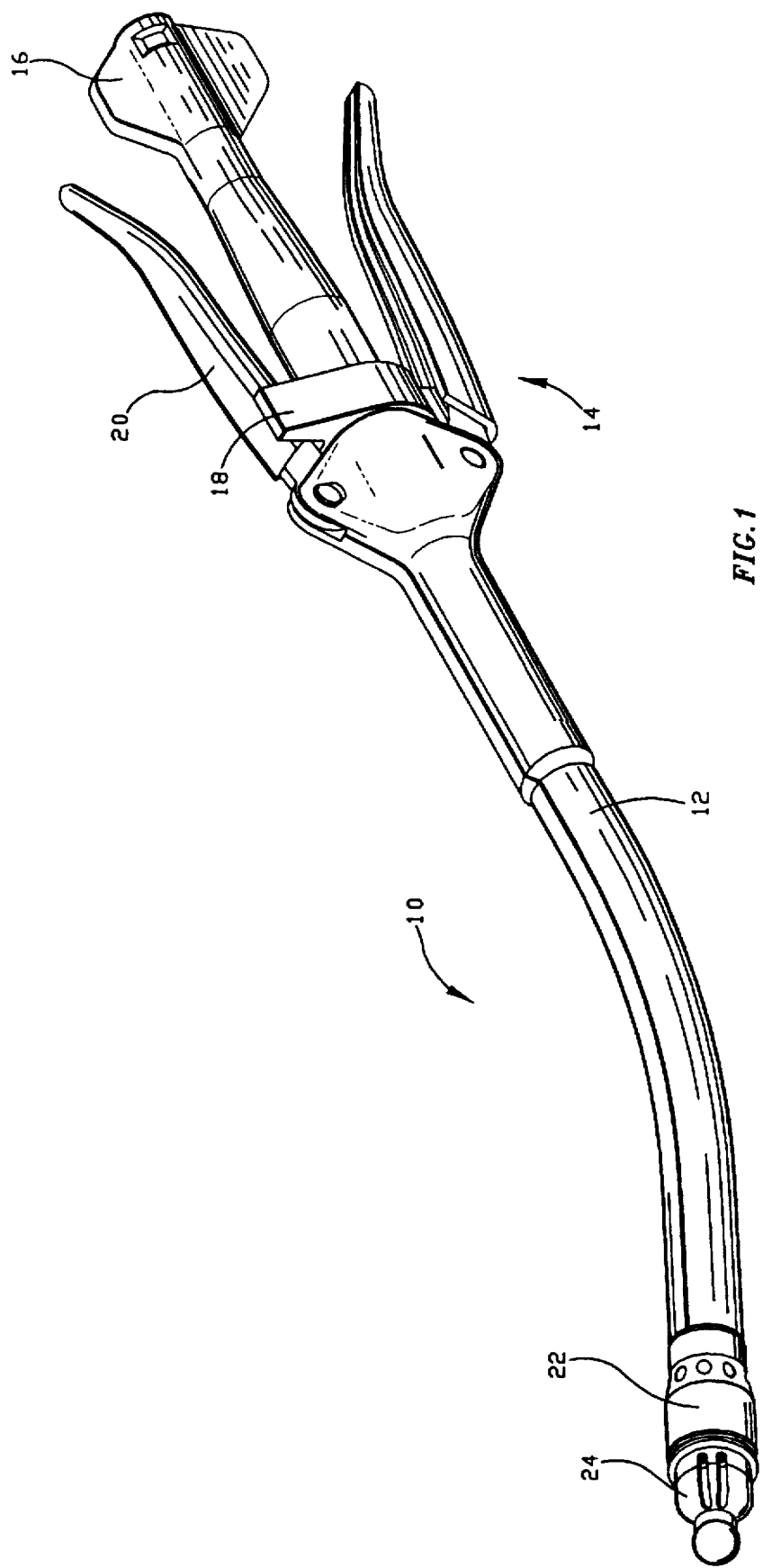
FIG. 1 is a perspective view of an instrument constructed according to the present invention for applying surgical fasteners to tissue.

Referring now in specific detail to the drawings, in which like reference numerals identify similar or identical elements throughout the several views, and initially to FIG. 1, which shows one embodiment of the surgical instrument for applying a circular array of fasteners of the present invention illustrated in perspective view as instrument 10. Instrument 10 includes elongate body portion 12 and handle section 14. Handle section 14 includes anvil adjustment member 16, lever lockout or safety member 18 and fastener firing levers 20. Fastener head portion 22 and anvil member 24 are disposed at the distal end of body portion 12. Except where noted otherwise, the materials utilized in the components of the surgical instrument of the present invention generally include such materials as polycarbonate for housing sections and related components, and stainless steel for such components which transmit forces. One preferred polycarbonate material is LEXAN® brand polycarbonate available from General Electric Company. However, equivalent alternative materials will readily come to the mind of those skilled in the art.

Figure 2:
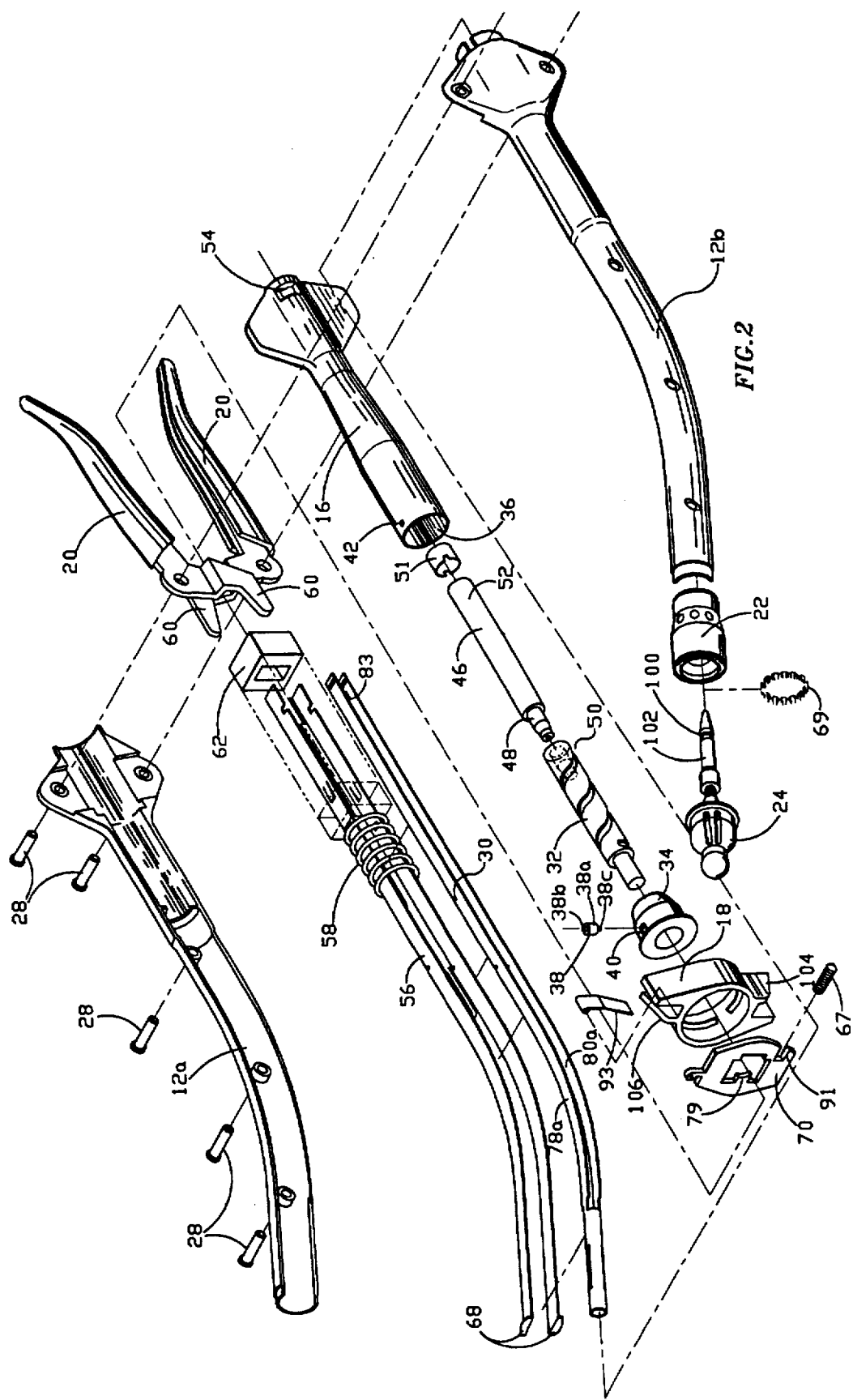
FIG. 2 is an exploded perspective view of an instrument in accordance with the present invention.

Referring now to FIG. 2, the various components of instrument 10 are shown in exploded view. Instrument 10 includes body or housing half sections 12a and 12b which are preferably molded and joined together by suitable fastening means such as rivets 28, or the like. To control axial movement of anvil member 24, elongated member 30 is slidably mounted within body portion 12, preferably by being securely mounted to helical cam member 32 by any suitable means such as, for example, welding or the like. Helical cam member 32 is slidably mounted within anvil adjustment member 16 by way of bushing 34 which is securely mounted in open end 36 of anvil adjustment member 16. Friction member 93 is disposed adjacent anvil adjustment member 16 to prevent relatively free rotation of the anvil adjustment member. In a preferred embodiment, both the mounting of bushing 34 and the camming of helical cam 32 is accomplished by compound pin 38 which has central portion 38a and extending portions 38b and 38c which are of reduced diameter. Portions 38a and 38b are press fitted into bores 40 and 42, respectively, located on bushing 34 and anvil adjustment member 16, respectively. Lower extending portion 38c serves as a camming pin and fits within the helical groove formed on the surface of helical cam 32. Anvil approximation indicator member 46 has extended portion 48 and is press fitted into proximal portion 50 of helical cam 32. Cap 51 is attached to proximal end 52 of anvil approximation indicator member 46. Cap 51 is preferably a colored piece which is easily visible through opening 54 formed near the proximal end of anvil adjustment member 16 to provide indication to the user when the anvil member is in the proper position for firing of the instrument. The distal end of elongated member 30 is provided with means to retain anvil member 24, which will be described in more detail below.

The fastener firing mechanism of instrument 10 includes fastener firing member 56 which is slidably mounted within body portion 12 preferably such that fastener firing member 56 is disposed around elongated member 30. Fastener firing member 56 is preferably biased in a proximal direction by suitable biasing means such as spring 58. Fastener firing levers 20 are pivotably mounted to body portion 12 and have extended portions 60 which cross over each other in scissor-like fashion. Bearing block 62 is mounted on fastener firing member 56, for example, being held between flexible finger portions 64 and raised portions 66 which are formed in the side walls of fastener firing member 56, as best illustrated in FIGS. 3 and 4. Fastener firing member 56 has bearing surfaces such as tabs 68 formed at the distal portion which serve to urge a pusher member within fastener head portion 22 in a distal direction in order to eject surgical fasteners 69, such as stainless steel or titanium staples, from fastener head portion 22.

Figures 12, 13, 13A:
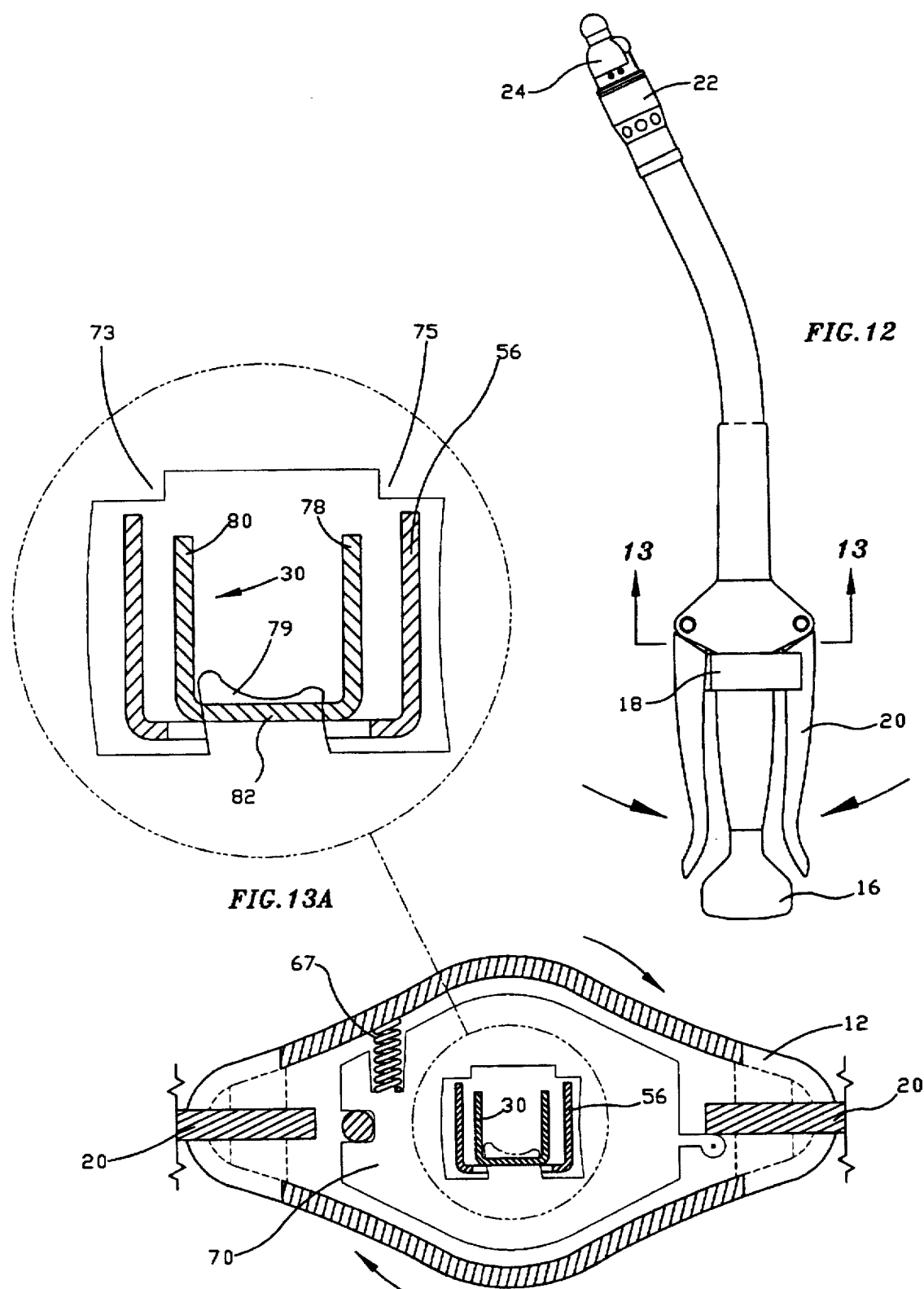
FIG. 12 is a plan view of the instrument showing the lever members in the fired position.
FIG. 13 is a cross-sectional view taken along section line 13—13 of FIG. 12.
FIG. 13A is an enlarged view of the area indicated on FIG. 13.

Also disposed on instrument 10 are lever lockout member 18 and elongate member lockout member 70. Lever lockout member 18 is preferably spring biased to the locked out position by spring 67 in slot 91. Each of these lockout members are preferably mounted on instrument 10 in such a manner that they are fixed relative to each other and upon pivoting of lever lockout member 18, elongate member lockout member 70 also pivots. With reference to FIGS. 11A and 13A, elongate member lockout member 70 has shoulder portions 73 and 75 formed therein as well as inwardly extending tab 79. The function of each of these portions of elongate member lockout member 70 will be described in further detail later herein.

Referring now to FIGS. 3–9, the structural and functional details of fastener firing member 56 and elongated member 30 will now be described in detail. In FIGS. 3–5, fastener firing member 56 is shown as preferably being a generally U-shaped member formed from material which can transmit forces effectively and reliably such as stainless steel. Fastener firing member 56 has side walls 72 and 74 which are connected by web 76. To fit fastener firing member 56 within the curved section of body portion 12, fastener firing member 56 has extended portions or flexible bands 72a and 74a which are preferably formed integrally with walls 72 and 74, respectively. Band 72a is shorter than band 74a. The difference in the length of the two bands corresponds to the amount of curvature of body portion 12 so that when fastener firing member 56 is mounted in body portion 12, the surfaces of tabs 68 form a plane parallel with the surface of the fastener pusher member (not shown).

Referring to FIGS. 6–9, elongated member 30 is shown as a U-shaped member, similar to fastener firing member 56. Elongated member 30 has side walls 78 and 80 which are joined by web 82. However, the cross-section dimensions of elongated member 30 are preferably such that elongated member 30 readily fits within fastener firing member 56. This arrangement is desirable so that elongated member 30 and fastener firing member 56 can slide independent of each other. As with fastener firing member 56, elongated member 30 must also be formed to fit within the curved contour of body portion 12. To accomplish this curvature, elongated member 30 has extended portions or flexible bands 78a and 80a which are preferably formed integrally with walls 78 and 80, respectively. Similar to the construction of fastener firing member 56, bands 78a and 80a of elongated member 30 are of different length. Elongated member 30 terminates at a distal end in a pair of opposed anvil retaining portions 84 and 86. Preferably, structure can be provided within body portion 12 (not shown) that serves to retain the side walls and bands of both elongated member 30 and fastener firing member 56. Such structure can be of unitary construction and have grooves to direct longitudinal movement of the channels and bands. Additionally, one or more seals (not shown) can be disposed within body portion 12 to prevent the flow of gases therethrough.

To facilitate retaining anvil member 24, and in particular, the anvil shaft therein, anvil retaining portions 84 and 86 are preferably semi-circular in shape as best illustrated in the cross-section view of FIG. 8. To assist in retention of anvil 24, anvil retaining portions 84 and 86 are provided with flexible finger portions 88 and 90, respectively, each of which have a raised portion formed thereon, such as camming and retaining portions 92 and 94, respectively. Camming surfaces 96 and 98 formed by camming and retaining portions 92 and 94, respectively serve to cam flexible finger portions 88 and 90 radially outward upon insertion of the anvil into the distal end of instrument 10. Referring temporarily back to FIG. 2, once annular groove portion 100 of anvil shaft 102 passes between retaining portions 84 and 86, flexible finger portions 88 and 90 return toward their initial or at rest state so that retaining portions 92 and 94 seat in annular groove 100.

In a preferred embodiment, extended portions 78a and 80a of elongated member 30 are preferably bent until the ends of anvil retaining portions 84 and 86 are aligned and are then permanently joined together (as shown in FIG. 2), by suitable bonding techniques, such as, by welding.

At the proximal end of elongated member 30, cut out portion 83 is formed to receive elongate lockout member 70 when elongated member is properly positioned for firing the staples of instrument 10. As best illustrated in FIGS. 6 and 7, cutout portion 83 is preferably formed through most of web 82 and continues partially up side wall 80.

The basic steps of operation are set forth in several patents, such as U.S. Pat. No. 4,576,167 issued to Noiles, U.S. Pat. No. 5,005,749 issued to Aranyi, and U.S. Pat. No. 5,119,983 to Green et al. the contents of each of these references are hereby incorporated by reference.

With reference to the instrument of the present invention, the user positions the tissue to be joined between anvil 24 and fastener head portion 22. Anvil adjustment member 16 is rotated to move elongated member 30 and anvil 24 proximally until the user sees approximation indicator 46 appear in opening 54 of anvil adjustment member 16. During this step, elongate member 30 acts as a tension member as it pulls anvil 24 into position adjacent fastener head portion 22. Prior to alignment of cut out 83 in elongate member 30 and extended portion 79 of elongate member lockout 70, lockout 70 is prevented from pivoting by contact between extended portion 79 and elongate member 30. When cut out 83 is positioned adjacent extended portion 79 of elongate member lockout 70, as further described below, lever lockout member 18 and elongate member lockout 70 are able to be pivoted by depressing, usually with the thumb, on lever lockout member 18. Once lever lockout member 18 is pivoted by the user, fastener firing levers 20 are depressed to urge fastener firing member 56 in a distal direction. This motion is accomplished by the camming effect of extended portions 60 of fastener firing levers 20 on bearing block 62 the distal movement of fastener firing member 56 urges fastener pusher members to eject fasteners 69 from fastener head portion 22. During this step, fastener firing member 56 acts as a compression member as it ejects fasteners 69.

With the above operational description of instrument 10 as a general base of the overall operation, the operation of elongate member lockout 70 will now be described in detail with reference to FIGS. 10–13. Once the user has instrument 10 inserted and the tissue to be joined is properly situated about the distal end of the instrument, anvil 24 is approximated to its proper position by rotation of anvil adjustment member 16, instrument 10 is positioned for firing, as shown in FIG. 10. In that position, however, fastener firing member 56 is still blocked from movement due to lever lockout member 18 still being oriented in the "safety on" position, i.e., lever locking extended portions 104 and 106 (FIG. 2) are aligned with the structure of levers 20 so that they cannot be depressed. Pivoting of lever lockout member 18 is prevented when elongated member 30 is out of the desired approximation range for firing the staples.

With reference to FIGS. 2–7, 11 and 13, prevention of the ability to pivot lever lockout member member 18 is accomplished by the relative position of elongated member 30 and thus the approximation of anvil 24. When anvil 24 is not properly approximated, side wall 80 and web 82 of elongated member 30 prevent extended portion 79 of elongate member lockout 70 from moving further inward (FIG. 11). However, once elongated member 30 is properly positioned, i.e., cut out 83 is aligned with extended portion 79 of elongate member lockout 70, then lever lockout member 18 which is fixedly secured to elongate member lockout member 70, can be pivoted, as shown in FIG. 13. When lockout 70 is pivoted, shoulder portions 73 and 75 of lockout 70 are moved out of notches 77 of fastener firing member 56 (FIGS. 3 and 4). This enables fastener firing levers 20 to be pivoted toward each other as shown in FIG. 12, thereby moving fastener firing member 56 distally and ejecting fasteners 69 from fastener head portion 22. As can be seen in FIGS. 13 and 13A once lever lockout 18, and elongate member lockout 70 are pivoted by the user, inwardly extending portion 79 of lockout 70 enters into cut out 83 (FIGS. 6 and 7) and blocks elongated member 30 from movement in either a proximal or distal direction.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical instrument for applying at least one circular array of fasteners, comprising:

a housing having proximal and distal end portions;

a shaft extending from said housing distal end portion, said shaft having proximal and distal end portions;

a fastener carrying cartridge positioned at said shaft distal end portion, said cartridge having a plurality of fasteners disposed therein;

a fastener firing member operatively associated with said fastener carrying cartridge;

at least one lever extending from said housing, said lever being adapted to move said fastener firing member to expel said fasteners from said cartridge;

an anvil, including an anvil shaft, disposed opposite said cartridge;

an elongated member operatively associated with said anvil for moving said anvil relative to said cartridge; and a lockout member operatively associated with said elongated member and said fastener firing member and movable between at least a first position and a second position such that when said lockout member is in said first position said lockout member permits operative movement of said elongated member and said anvil and prevents said fastener firing member from firing said plurality of fasteners and when said lockout member is in said second position said lockout member prevents operative movement of said elongated member and permits movement of said fastener firing member sufficient to fire said plurality of fasteners.

2. A surgical instrument as recited in claim 1, further comprising a safety member operatively associated with said at least one lever member operatively associated with said at least one lever and movable between at least a first position and a second position such that when said safety member is in said first position said at least one lever is operatively movable and when said safety member is in said second position said at least one lever is prevented from operatively moving.

3. A surgical instrument as recited in claim 2, wherein said safety member is operatively associated with said lockout member.

4. A surgical instrument as recited in claim 1, wherein said shaft is tubular.

5. A surgical instrument as recited in claim 1, wherein said shaft is curved.

6. A surgical instrument as recited in claim 1, wherein said fasteners are surgical staples.

7. A surgical instrument as recited in claim 1, wherein said lockout member is biased to remain initially in said first position.

8. A surgical instrument as recited in claim 1, wherein said elongated member includes a pair of extended portions at a distal end thereof, said pair of extended portions adapted for retaining said shaft of said anvil assembly.

9. A surgical instrument as recited in claim 8, wherein said pair of extended portions are arcuately shaped.

10. A surgical instrument as recited in claim 8, wherein said pair of extending portions include releasable retaining means disposed thereon for releasably retaining said anvil assembly.

11. A surgical instrument as recited in claim 8, wherein said pair of extended portions include at least one resilient prong adapted to retain said anvil assembly.

12. A surgical instrument as recited in claim 1, wherein a portion of said elongated member is U-shaped, having at least two side wall portions connected by a web portion.

13. A surgical instrument as recited in claim 12, wherein said at least two side wall portions are parallel.

14. A surgical instrument as recited in claim 12, wherein said elongated member includes at least two finger portions extending from a distal end thereof, said finger portions adapted to retain said anvil assembly.

15. A surgical instrument as recited in claim 14, wherein said at least two finger portions are flexible.

16. A surgical instrument as recited in claim 15, wherein said at least two finger portions are of a predetermined unequal length such that upon curving said at least two finger portions a predetermined amount of curvature end portions of said at least two finger portions become aligned with each other.

17. A surgical instrument for applying at least one circular array of fasteners, comprising:

a body portion;

a fastener head portion connected to said body portion and including a plurality of fasteners;

an elongated member longitudinally disposed within said body portion;

at least one movable lever member operatively associated with said body portion to fire said fasteners;

an anvil assembly, including an anvil head portion and an anvil shaft portion operatively associated with said elongated member such that movement of said elongated member from a first position to a second position imparts movement of said anvil assembly relative to said fastener head portion, said anvil head portion adapted to form said plurality of fasteners; and a lockout member movable between at least a first position and a second position wherein when said lockout member is disposed in said first position said elongated member is permitted to move longitudinally within said body portion and when said lockout member is disposed in said second position said elongated member is held in a fixed position and said anvil head portion is held at a predetermined fixed longitudinal distance from said fastener head portion.

18. A surgical instrument as recited in claim 17, wherein said lockout member is pivotably disposed within said body portion.

19. A surgical instrument as recited in claim 17, wherein said lockout member is biased to remain initially in said first position.

20. A surgical instrument as recited in claim 17, wherein said elongated member includes a pair of extended portions at a distal end thereof, said pair of extended portions adapted for retaining a shaft of said anvil assembly.

21. A surgical instrument as recited in claim 20, wherein said pair of extended portions are arcuately shaped.

22. A surgical instrument as recited in claim 20, wherein said pair of extended portions include releasable retaining means disposed thereon for releasably retaining said anvil assembly.

23. A surgical instrument as recited in claim 20, wherein said pair of extended portions include at least one resilient prong adapted to retain said anvil assembly.

24. A surgical instrument as recited in claim 17, wherein said elongated member is at least partially U-shaped having at least two side wall portions connected by a web portion.

25. A surgical instrument as recited in claim 24, wherein said at least two side wall portions are parallel.

26. A surgical instrument as recited in claim 17, wherein said elongated member includes at least two finger portions extending from a distal end thereof, said finger portions adapted to retain said anvil assembly.

27. A surgical instrument as recited in claim 26, wherein said at least two finger portions are arcuately shaped.

28. A surgical instrument as recited in claim 17 further comprising a fastener firing member operatively associated with said fastener head portion and said at least one lever member, said fastener firing member being adapted to eject said fasteners from said fastener firing member.

29. A surgical instrument as recited in claim 28, wherein said fastener firing member is at least partially U-shaped having at least two side wall portions connected by a web portion.

30. A surgical instrument as recited in claim 29, wherein said at least two side wall portions are parallel.

31. A surgical instrument as recited in claim 28, wherein said fastener firing member is held in a fixed position when said locking member is in said first position.

32. A surgical instrument for applying at least one circular array of fasteners, comprising:

a body portion including a proximal end and a distal end, the body portion having a handle section at the proximal end and an elongated housing section extending from the distal end;

a fastener head portion connected to said body portion and including a plurality of fasteners;

at least one movable lever member associated with said handle section and operatively connected to said fastener head portion;

an elongated U-shaped member forming an open sided channel section along a portion thereof, the elongated U-shaped member extending from said handle section and at least partially through said elongated housing section and having at least two finger portions extending from a distal end thereof, said U-shaped member being movable between a first position and a second position;

an anvil member attached to said at least two finger portions of said elongated U-shaped member, said anvil member being adapted for forming said plurality of fasteners.

33. A surgical instrument as recited in claim 32, wherein said anvil member is removably attached to said at least two finger portions.

34. A surgical instrument as recited in claim 32, wherein said at least two finger portions have an arcuate cross section shape.

35. A surgical instrument as recited in claim 32, further comprising locking means operatively associated with said U-shaped member and movable between at least a first position wherein said U-shaped member is operatively movable and a second position wherein said U-shaped member is prevented from being operatively movable.

36. A surgical instrument as recited in claim 35, wherein said locking means is further operatively associated with said at least one movable lever member such that when said locking means is in said first position, said U-shaped member is movable and said plurality of fasteners is prevented from being expelled from said fastener head portion and when said locking means is in said second position, said U-shaped member is locked and said plurality of fasteners are expellable from said fastener head portion.

37. A surgical instrument as recited in claim 36, wherein said locking means is biased to remain initially in said first position.

38. A surgical instrument for applying at least one circular array of fasteners, comprising:

a body portion including a handle section at a proximal end thereof;

a fastener head portion connected to said body portion, said fastener head portion configured and dimensioned to apply at least one circular array of fasteners;

at least one movable lever member operatively associated with said handle section;

an elongated U-shaped compression member having a major and minor axis forming a channel section having a laterally directed open side along the major axis, the compression member being operatively connected at a proximal end to said at least one movable lever member, the compression member being further operatively connected at a distal end to said fastener head portion; and an elongated U-shaped tension member which extends from said handle section to a distal portion of said body portion and is slidably disposed adjacent said compression member.

39. A surgical instrument for applying at least one circular array of fasteners, comprising:

a body portion;

a fastener head portion connected to said body portion and including a plurality of fasteners;

an elongate member disposed within said body portion;

an actuator operatively associated with said body portion to fire said plurality of fasteners;

an anvil, including a head portion and a shaft portion, said anvil being operatively connected to said elongate member such that movement of said elongated member from a first position to a second position imparts movement of said anvil relative to said fastener head portion; and a lockout member operatively associated with said anvil and movable between at least a first position and a second position, wherein when said lockout member is disposed in said first position said elongate member is permitted to move longitudinally within said body portion and when said lockout member is disposed in said second position said elongate member is restricted from operative longitudinal movement within said body portion.

* * * * *